US012220590B2

(12) United States Patent
Ries et al.

(10) Patent No.: US 12,220,590 B2
(45) Date of Patent: *Feb. 11, 2025

(54) FEEDTHROUGH ASSEMBLY AND DEVICE INCLUDING SAME

(71) Applicant: Medtronic, Inc., Minneapolis, MN (US)

(72) Inventors: Andrew J. Ries, Lino Lakes, MN (US); Chunho Kim, Phoenix, AZ (US); Robert A. Munoz, Andover, MN (US); Christopher T. Kinsey, East Bethel, MN (US); Jeffrey Voss, White Bear Lake, MN (US); Kris A. Peterson, Edina, MN (US); Mark E. Henschel, Phoenix, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/124,706

(22) Filed: Mar. 22, 2023

(65) Prior Publication Data

US 2023/0218911 A1    Jul. 13, 2023

Related U.S. Application Data

(63) Continuation of application No. 17/125,250, filed on Dec. 17, 2020, now Pat. No. 11,633,611.

(Continued)

(51) Int. Cl.
*A61N 1/375*    (2006.01)

(52) U.S. Cl.
CPC ....... *A61N 1/3754* (2013.01); *A61N 1/37512* (2017.08); *A61N 1/3756* (2013.01)

(58) Field of Classification Search
CPC .............. A61N 1/3754; A61N 1/37512; A61N 1/3756; A61N 1/37205
See application file for complete search history.

(56) References Cited

U.S. PATENT DOCUMENTS

| 8,162,684 B1 | 4/2012 | Sochor |
| 10,124,559 B2 | 11/2018 | Sandlin et al. |

(Continued)

FOREIGN PATENT DOCUMENTS

| WO | WO 2020/025363 | 2/2020 |

*Primary Examiner* — Catherine M Voorhees
(74) *Attorney, Agent, or Firm* — Mueting Raasch Group

(57) ABSTRACT

Various embodiments of a feedthrough header assembly and a device including such assembly are disclosed. The assembly includes a header having an inner surface and an outer surface; a dielectric substrate having a first major surface and a second major surface, where the second major surface of the dielectric substrate is disposed adjacent to the inner surface of the header; and a patterned conductive layer disposed on the first major surface of the dielectric substrate, where the patterned conductive layer includes a first conductive portion and a second conductive portion electrically isolated from the first conductive portion. The assembly further includes a feedthrough pin electrically connected to the second conductive portion of the patterned conductive layer and disposed within a via that extends through the dielectric substrate and the header. The feedthrough pin extends beyond the outer surface of the header.

24 Claims, 11 Drawing Sheets

Related U.S. Application Data

(60) Provisional application No. 62/950,694, filed on Dec. 19, 2019.

(56) References Cited

U.S. PATENT DOCUMENTS

| | | |
|---|---|---|
| 2006/0247711 A1 | 11/2006 | Verhoef et al. |
| 2015/0157861 A1 | 6/2015 | Aghassian |
| 2015/0321012 A1 | 11/2015 | Cinbis et al. |
| 2016/0151621 A1 | 6/2016 | Maile |
| 2016/0184593 A1 | 6/2016 | Ruben et al. |
| 2018/0304084 A1* | 10/2018 | Stevenson .............. H01R 4/022 |
| 2018/0333586 A1* | 11/2018 | Wasson ................ A61B 5/0031 |
| 2019/0030346 A1* | 1/2019 | Li ........................ A61N 1/3702 |
| 2019/0184179 A1 | 6/2019 | Stahmann et al. |
| 2020/0155860 A1* | 5/2020 | Keller .................. A61N 1/3756 |
| 2021/0178518 A1 | 6/2021 | Ruben et al. |
| 2021/0308473 A1 | 10/2021 | Doerr |

\* cited by examiner

FEEDTHROUGH ASSEMBLY AND DEVICE INCLUDING SAME

CROSS-REFERENCE TO RELATED APPLICATIONS

This application is a continuation of application Ser. No. 17/125,250, filed Dec. 17, 2020, and which claims the benefit of U.S. Provisional Application No. 62/950,694, filed Dec. 19, 2019, the disclosures of which being incorporated by reference herein in their entireties.

TECHNICAL FIELD

This disclosure generally relates to a feedthrough header assembly and in particular an implantable medical device that includes the feedthrough header assembly.

BACKGROUND

Implantable medical devices such as an implantable pacemaker can deliver pacing pulses to a patient's heart and monitor conditions of the patient's heart. In some examples, the implantable pacemaker includes a pulse generator and one or more electrical leads. The pulse generator may, for example, be implanted in a small pocket in the patient's chest. The electrical leads can be coupled to the pulse generator, which may contain circuitry that generates pacing pulses and/or senses cardiac electrical activity. The electrical leads may extend from the pulse generator to a target site (e.g., an atrium and/or a ventricle) such that electrodes at the distal ends of the electrical leads are positioned at the target site. The pulse generator may provide electrical stimulation to the target site and/or monitor cardiac electrical activity at the target site via the electrodes.

Other implantable pacemakers are configured to be implanted entirely within a chamber of the heart. Such pacemakers can be referred to as intracardiac pacing devices or leadless pacing devices, and can include one or more electrodes on their outer housings to deliver therapeutic electrical signals and/or sense intrinsic depolarizations of the heart. Such pacemakers can be positioned within or outside of the heart and, in some examples, can be anchored to a wall of the heart via a fixation mechanism.

SUMMARY

The techniques of this disclosure generally relate to a feedthrough header assembly and an implantable medical device that includes such assembly. The assembly can include a header and a dielectric substrate that includes a patterned conductive layer, where the dielectric substrate electrically isolates the patterned conductive layer from the header. The assembly can also include a feedthrough pin that is electrically connected to a conductive portion of the patterned conductive layer. The feedthrough pin extends through the dielectric substrate and the header and beyond an outer surface of the header while maintaining isolation from the header. The feedthrough header assembly can form a part of an electronics module. Such electronics module can be electrically connected to a power source to provide an implantable medical device.

In one example, aspects of this disclosure relate to a feedthrough header assembly that includes a header having an inner surface and an outer surface, and a dielectric substrate having a first major surface and a second major surface. The second major surface of the dielectric substrate is disposed adjacent to the inner surface of the header. The assembly further includes a patterned conductive layer disposed on the first major surface of the dielectric substrate, where the patterned conductive layer includes a first conductive portion and a second conductive portion electrically isolated from the first conductive portion. The assembly further includes a feedthrough pin electrically connected to the second conductive portion of the patterned conductive layer and disposed within a via that extends through the dielectric substrate and the header. The feedthrough pin extends beyond the outer surface of the header.

In another example, aspects of this disclosure relate to an electronics module that includes an electronic layer having a substrate and an electronic component disposed on the substrate, and a feedthrough header assembly electrically connected to the electronic layer. The feedthrough header assembly includes a header having an inner surface and an outer surface, and a dielectric substrate having a first major surface and a second major surface. The second major surface of the dielectric substrate is disposed adjacent to the inner surface of the header. The assembly further includes a patterned conductive layer disposed on the first major surface of the dielectric substrate, where the patterned conductive layer includes a first conductive portion and a second conductive portion electrically isolated from the first conductive portion. The assembly also includes a feedthrough pin electrically connected to the second conductive portion of the patterned conductive layer and disposed within a via that extends through the dielectric substrate and the header. The feedthrough pin extends beyond the outer surface of the header.

In another example, aspects of this disclosure relate to an implantable medical device that includes a power source and an electronics module electrically connected to the power source the electronics module includes an electronic layer and a feedthrough header assembly electrically connected to the electronic layer. The electronic layer includes a substrate and an electronic component disposed on the substrate. The feedthrough header assembly includes a header having an inner surface and an outer surface, and a dielectric substrate having a first major surface and a second major surface. The second major surface of the dielectric substrate is disposed adjacent to the inner surface of the header. The feedthrough header assembly further includes a patterned conductive layer disposed on the first major surface of the dielectric substrate, where the patterned conductive layer includes a first conductive portion and a second conductive portion electrically isolated from the first conductive portion. The feedthrough header assembly further includes a feedthrough pin electrically connected to the second conductive portion of the patterned conductive layer and disposed within a via that extends through the dielectric substrate and the header. The feedthrough pin extends beyond the outer surface of the header.

In another example, aspects of this disclosure relate to a method that includes disposing a patterned conductive layer on a first major surface of a dielectric substrate, where the patterned conductive layer includes a first conductive portion and a second conductive portion. The method further includes electrically connecting a feedthrough pin to the second conductive portion of the patterned conductive layer, and disposing a second major surface of the dielectric substrate adjacent to an inner surface of a header such that the feedthrough pin is disposed within a via and the feedthrough pin extends through the dielectric substrate, the header, and beyond an outer surface of the header.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The techniques of this disclosure generally relate to a feedthrough header assembly and an implantable medical device that includes such assembly. The assembly can include a header and a dielectric substrate that includes a patterned conductive layer, where the dielectric substrate electrically isolates the patterned conductive layer from the header. The assembly can also include a feedthrough pin that is electrically connected to a conductive portion of the patterned conductive layer. The feedthrough pin extends through the dielectric substrate and the header and beyond an outer surface of the header while maintaining isolation from the header. The feedthrough header assembly can form a part of an electronics module. Such electronics module can be electrically connected to a power source to provide an implantable medical device.

Typical header assemblies of implantable medical devices can include a feedthrough pin that is electrically connected to an electronics module disposed within a housing of the device. The feedthrough pin can extend from inside the housing and beyond a header that is connected to the housing. Because one or both of the housing or the header can be electrically active, the feedthrough pin is typically electrically isolated from both the header and the housing. An opening in the header and the housing through which the feedthrough pin extends must be sealed such that body fluids and contaminants do not flow into an interior of the housing where they can damage electronic components.

One or more embodiments of the present disclosure can provide a feedthrough header assembly that includes a feedthrough pin that can be connected to an electronics module disposed within a housing of a device, where the feedthrough pin is electrically connected to the module in a reliable manner while efficiently utilizing space within the housing. The feedthrough header assembly can be a solderable component or subassembly that is compatible with various standard surface mount processing and connects to an integrated circuit or die stack in a reliable and volumetrically efficient manner.

Figure 1:
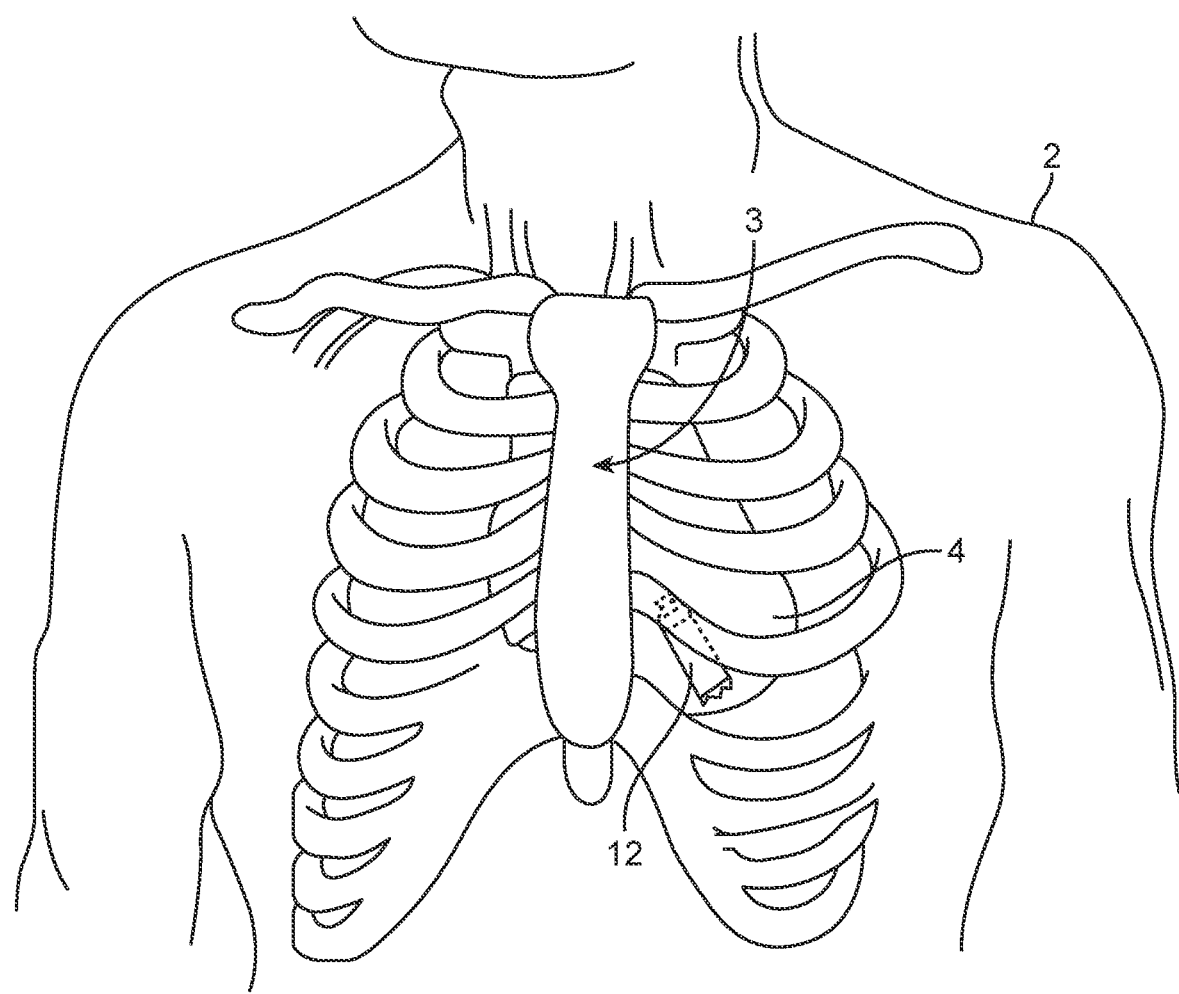
FIG. 1 is a schematic view of one embodiment of an implantable medical device disposed within a body of a patient.

FIG. 1 is a schematic view of one embodiment of an implantable medical device 12 (IMD) disposed within a body of a patient 2. The IMD 12 can include any suitable medical device, e.g., a pacing device, pressure sensing device, cardiac monitor, other physiologic sensor, etc. The IMD 12 can include an arrangement of an electronics module and a feedthrough header assembly as is further described herein. IMD 12 can be, for example, an implantable leadless pacing device that is configured for implantation entirely within one of the chambers of a heart 4 and that provides electrical signals to the heart beneath a sternum 3 via electrodes carried on the housing of pacing device.

IMD 12 is generally described as being attached within a chamber of the heart 4 as an intracardiac pacing device. In one or more embodiments, IMD 12 can be attached to an external surface of the heart 4, such that the device is disposed outside of the heart but can pace a desired chamber. In one or more embodiments, IMD 12 is attached to an external surface of the heart 4 and one or more components of the device can be in contact with an epicardium of the heart. The IMD 12 is schematically shown in FIG. 1 attached to a wall of a ventricle of the heart 4 via one or more fixation elements (e.g. tines, helix, etc.) that penetrate the tissue. These fixation elements can secure the IMD 12 to the cardiac tissue and retain an electrode (e.g., a cathode or an anode) in contact with the cardiac tissue. IMD 12 can be implanted at or proximate to the apex of the heart. In one or more embodiments, a pacing device may be implanted at other ventricular locations, e.g., on the free-wall or septum, an atrial location, or any location on or within the heart 4.

Figure 2:
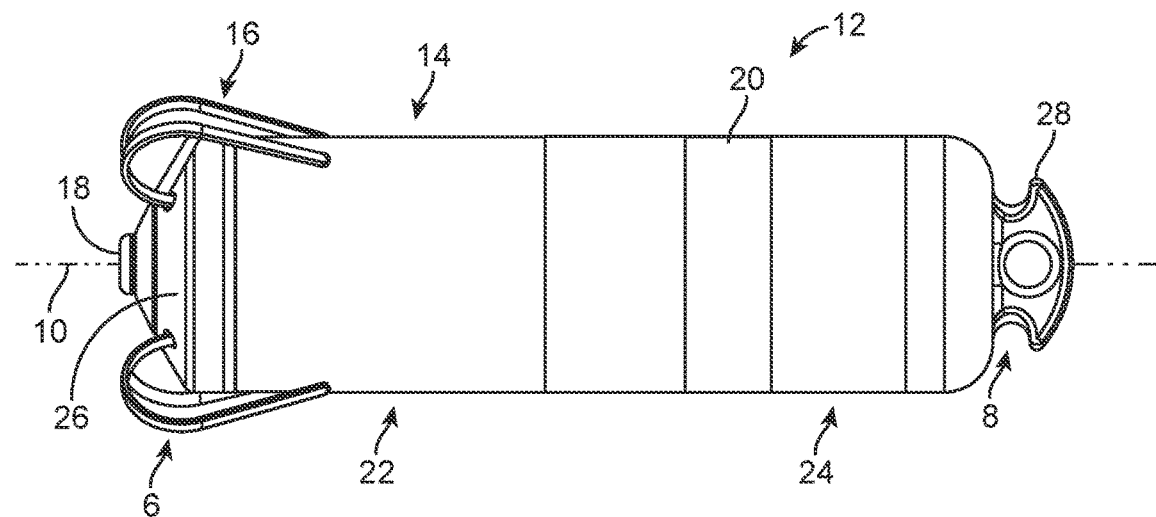
FIG. 2 is a schematic perspective view of the implantable medical device of FIG. 1.

FIG. 2 is a schematic side view of the IMD 12 of FIG. 1. In one or more embodiments, the IMD 12 is adapted to be implanted within a chamber of the heart 4 of the patient 2, e.g., to monitor electrical activity of the heart and/or provide electrical therapy to the heart. In the example shown in FIG. 2, the IMD 12 includes a housing 14, fixation tines 16, and electrodes 18 and 20.

The housing 14 of the IMD 12 can include any suitable dimensions and take any suitable shape or shapes. The housing 14 extends between a first end 6 and a second end 8 along a longitudinal axis 10. In one or more embodiments, the housing 14 can have a cylindrical (e.g., pill-shaped) form factor. In one or more embodiments, the housing 14 includes an elongated tubular housing. Further, the housing 14 can include any suitable material or materials as is further described herein.

The IMD 12 can include a fixation mechanism adapted to fix pacing device 12 to tissue within the body of the patient 2. For example, in the embodiment illustrated in FIG. 2, the IMD 12 includes fixation tines 16 extending from the housing 14 that are adapted to engage with tissue to substantially fix a position of the housing within the patient 2. In one or more embodiments, the fixation tines 16 are adapted to anchor housing 14 to the cardiac tissue such that pacing device 12 moves along with the cardiac tissue during cardiac contractions. Fixation tines 16 can include any suitable material or materials, e.g., a shape memory material (e.g., Nitinol). Although the IMD 12 includes a plurality of fixation tines 16 that are adapted to anchor the device to tissue, in one or more embodiments, the device can be fixed to tissue using other types of fixation mechanisms, such as, but not limited to, barbs, coils, and the like.

Housing 14, also referred to as an elongated housing, houses electronic components of the IMD 12, e.g., sensing circuitry for sensing electrical activity via electrodes 18 and 20 and therapy generation circuitry for delivering electrical stimulation therapy via the electrodes. Electronic components can include any discrete and/or integrated electronic circuit components that implement analog and/or digital circuits capable of producing the functions attributed to the IMD 12 described herein. In one or more embodiments, housing 14 can also house components for sensing other physiological parameters, such as acceleration, pressure, sound, and/or impedance. Although shown with two electrodes 18 and 20, the device 12 can include any suitable number of electrodes disposed in any suitable portion or portions of the housing.

Additionally, the housing 14 can also house a memory that includes instructions that, when executed by processing circuitry housed within housing, cause the IMD 12 to perform various functions attributed to the device herein. In one or more embodiments, the housing 14 can house communication circuitry that enables the IMD 12 to communicate with other electronic devices, such as a medical device programmer. In one or more embodiments, the housing 14 can house an antenna for wireless communication. The housing 14 can also house a power source, such as a battery. The housing 14 can be hermetically or near-hermetically sealed using any suitable technique or techniques to help prevent fluid ingress into housing. For example, in one or more embodiments, one or more portions of the housing 14 can be hermetically sealed together utilizing one or more laser diffusion bonding techniques described in co-owned U.S. Pat. No. 10,124,559 B2, entitled KINETICALLY LIMITED NANO-SCALE DIFFUSION BOND STRUCTURES AND METHODS.

The IMD 12 include the electrodes 18, 20 that can be connected to the housing utilizing any suitable technique or techniques. In one or more embodiment, at least one of the electrodes 18, 20 can be mechanically connected to housing 14. In one or more embodiments, at least one of the electrodes 18, 20 can be defined by an outer portion of the housing 14 that is electrically conductive. For example, electrode 20 can be defined by a tissue-exposed conductive portion of housing 14.

Electrodes 18, 20 are electrically isolated from each other. Electrode 18 can be referred to as a tip electrode, and fixation tines 16 can be adapted to anchor the IMD 12 to tissue such that electrode 18 maintains contact with the tissue. In one or more embodiments, fixation tines 16 can also be electrically connected to one or more electronic components such that the tines are adapted to direct an electrical signal to tissue of the patient and/or receive an electronic signal from the tissue. In one or more embodiments, a portion of housing 14 can be covered by, or formed from, an insulative material to isolate electrodes 18 and 20 from each other and/or to provide a desired size and shape for one or both of electrodes.

Electrode 20 can be a portion of housing 14, e.g., second portion 24, that does not include such insulative material. Electrode 20 can be most or all of housing 14, but most of the housing (other than electrode 20) can be covered with an insulative coating. In one or more embodiments, electrode 20 may be coated with materials to promote conduction. In one or more embodiments, electrode 20 can be part of a separate ring portion of housing 14 that is conductive. Electrodes 18, 20, which may include conductive portion(s) of the first portion 22 of housing 14, can be electrically connected to at least some electronics of pacing device 12 (e.g., sensing circuitry, electrical stimulation circuitry, or both). In one or more embodiments, the housing 14 can include an end cap 26, which can house or enclose a feedthrough header assembly (e.g., feedthrough header assembly 42 of FIG. 3) to electrically connect the electrode 18 to the electronics within the housing 14, while electrically isolating the electrode from the housing 14, e.g., including electrode 20 or other conductive portions of the housing.

In the embodiment illustrated in FIG. 2, the housing 14 includes a first portion 22 and a second portion 24. The first portion 22 can be disposed adjacent to the first end 6 of the housing 14, and the second portion 24 can be disposed adjacent to the second end 8 of the housing. As used herein, the term "adjacent to the first end" means that an element or component is disposed closer to the first end 6 of the housing 14 than to the second end 8 of the housing. Further, the term "adjacent to the second end" means that an element or component is disposed closer to the second end 8 of the housing 14 than to the first end 6 of the housing. The second portion 24 can, in one or more embodiments, define at least part of a power source case that houses a power source (e.g., a battery) of the IMD 12. In one or more embodiments, the second portion 24 can include the conductive portion of the housing 14 that forms the electrode 20.

The second portion 24 of the housing can include a vent 35 disposed in any suitable location. The vent 35 can allow backfill gas exchange of the package device 12 before the first portion 22 is connected to the second portion. Once gas exchange is completed, the vent 35 can be sealed with a weld as is further described in U.S. patent application Ser. No. 17/118,283 to Ruben et al. and entitled HERMETIC ASSEMBLY AND DEVICE INCLUDING SAME.

The first portion 22 of the housing 14 can be connected to the second portion 24 of the housing using any suitable technique or techniques. In one or more embodiments, the first portion 22 of the housing 14 can be connected to the second portion 24 of the housing using laser bonding. For example, electromagnetic radiation (e.g., light) can be directed through an outer surface of the first portion 22 and focused at an interface between the first portion and the second portion 24 to form a laser bond.

Any suitable electromagnetic radiation can be utilized to form a bond between the first portion 22 and the second portion 24 of the housing 14. In one or more embodiments, the electromagnetic radiation can include laser light that can include any suitable wavelength or range of wavelengths. In one or more embodiments, the laser light can include light having a wavelength of at least 200 nm. In one or more embodiments, the laser light can include a wavelength of no greater than 10,000 nm. For example, laser light can include UV light, visible light, IR light, and combinations thereof. In one or more embodiments, a UV laser can be utilized to provide light having a wavelength of about 350 nm and a pulse width of 30 ns. In one or more embodiments, the materials for the first and second portions 22, 24 of the housing 14, and the power level and wavelength of the light used may be selected such that the light may not directly damage, ablate, warp, or cut the housing, and such that the first and second portions of the housing retain their bulk properties.

In general, light can be provided by any suitable laser or laser system. For example, the laser may generate light having a relatively narrow set of wavelengths (e.g., a single wavelength). The light emitted by the laser may form a collimated beam that may not be focused at a particular point. The light emitted by the laser may be focused at interfaces between the first portion 22 and the second portion 22 of the housing 14 to generate a laser bond.

Although the laser may provide light that has a narrow range of wavelengths, in one or more embodiments, the laser may represent one or more devices that emit light having a wider range of wavelengths than a single typical laser. A wide variety of devices may be used to emit light having a narrow or wide range of wavelengths. In one or more embodiments, the laser may include one or more laser devices including diode and fiber lasers. Laser sources may also include, e.g., TI sapphire, argon ion, Nd:YAG, XeF, HeNe, Dye, GaAs/AlGaAs, $CO_2$, Alexandrite, InGaAs, InGaAsP, Nd:glass, Yb:YAG, or Yb fiber lasers. The laser device may also include one of continuous wave, modulated, or pulsed modes. Accordingly, a wide variety of laser devices may be used in the bonding process. In one or more embodiments, a power level of the laser may be set to approximately 1 W, distributed across the approximate focused beam diameter of 10 μm, with a top hat or Gaussian spatial energy profile.

In the embodiment of FIG. 2, the IMD 12 can also include a flange 28 connected to the second portion 24 of the housing 14 at the second end 8 of the housing that defines an opening. The flange 28 can enable medical instruments to attach to the IMD 12, e.g., for delivery and/or extraction of the device. For example, a tether that extends through a catheter inserted into the heart 4 (FIG. 1) can be attached to the flange 28 and/or threaded through the opening to implant or extract the IMD 12.

Figure 3:
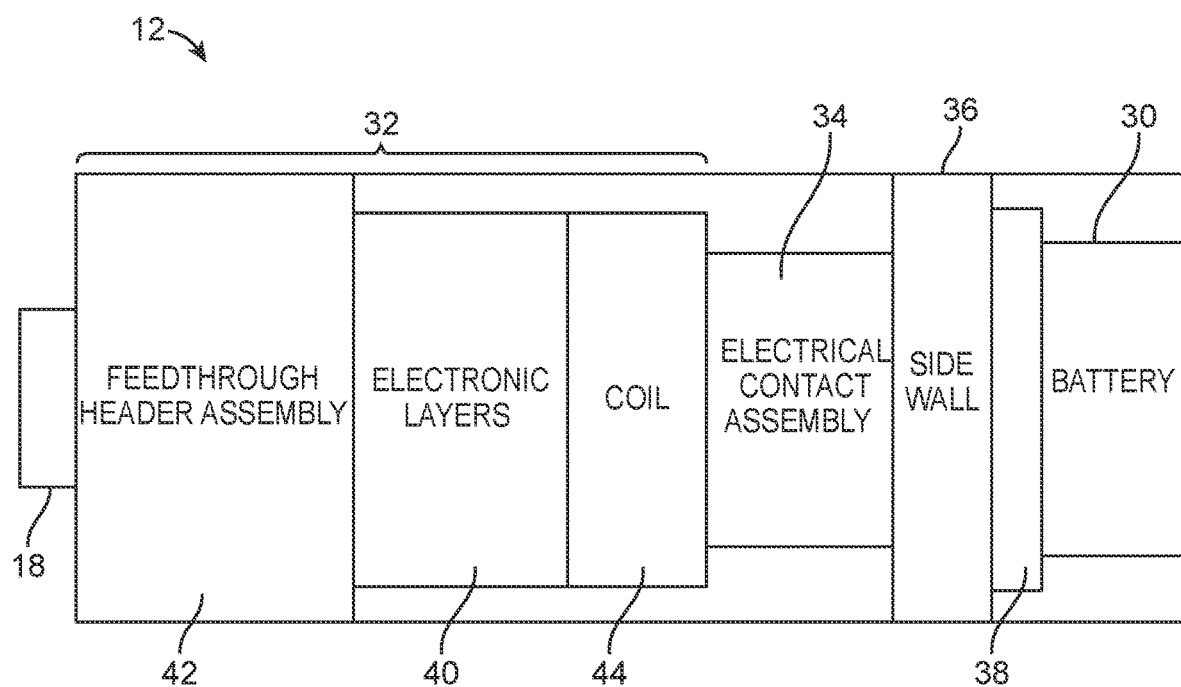
FIG. 3 is a schematic block diagram view of the implantable medical device of FIG. 1.

FIG. 3 is a schematic block diagram of one embodiment of the IMD 12 including a power source 30 (e.g., battery), an electronics module 32, and an electrical contact assembly 34. Although the IMD of FIG. 3 is described as IMD 12, the structures shown in FIG. 3 can also be used in other implantable or external medical devices, such as cardioverter-defibrillators, physiological monitors, or neurostimulators, or any other electronic devices.

The housing 14 includes the first and second portions 22, 24 and a side wall 36 disposed within the housing between the battery 30 and the electrical contact assembly 34. The side wall 36 can be disposed within the first and second housing portions 22, 24 or at the boundary of first and second housing portions. In one or more embodiments, the first and second housing portions 22, 24 are common with a ground terminal of battery 30. In one or more embodiments, one or both of the first and second housing portions 22, 24 is non-conductive. For example, first housing portion 22 can be formed of a non-conductive material, such as sapphire, which may allow easier transmission of electromagnetic signals into and out of the housing 14 than a metal or other conductive material would allow.

As shown in the embodiment illustrated in FIG. 3, the side wall 36 extends across housing 14 between the battery 30 on one side and electrical contact assembly 34 on the other side. The side wall 36 can include at least one feedthrough (not shown) to allow for electrical connection between the battery 30 and the electronics module 32. As discussed herein, feedthrough header assembly 42 can also include at least one feedthrough to allow for an electrical connection between electrode 18 and electronic layers 40. Electronics module 32 is disposed between the electrode 18 and electrical contact assembly 34. In one or more embodiments, electrical contact assembly 34 can be fixed to side wall 36 to provide mechanical support for the electronics module 32. The electronic contact assembly 34 provides an electrical connection between the battery 30 and the electronics module 32. For example, the electronics module 32 can include one or more electrical contacts that are adapted to electrically connect the module to the electronic contact assembly 34.

The IMD 12 can also include a battery header 38 disposed between the battery 30 and the electrical contact assembly 34. The side wall 36 can form part or all of the battery header 38. The battery header 38, the side wall 36, and the electrical contact assembly 34 can be electrically connected to the electronics module 32 using any suitable technique or techniques. In one or more embodiments, the battery header 38, the side wall 36, and/or electrical contact assembly 34 can include feedthroughs and/or openings for creating an electrical connection between the battery 30 and electronics module 32.

The electrical contact assembly 34 can include any suitable assembly for electrically connecting the electronics module 32 and the battery 30, e.g., one or more embodiments of electrical contact assemblies described in co-owned U.S. patent application Ser. No. 17/071,463, entitled ELECTRONICS ASSEMBLY FOR IMPLANTABLE MEDICAL DEVICE. In one or more embodiments, the electrical contact assembly 34 can include a spring contact for holding electronics module 32 in place and for providing electrical connections between the electronics module and the battery 30.

The IMD 12 can be manufactured utilizing a single tube for the first housing portion 22 or as two tube sections for such housing portion. Using a single tube for the housing portion 22, in contrast to two sections, e.g., two half-pipes, may lower the cost and complexity of the encasement for pacing device 12. A single tube opens up new encasement options and can be manufactured from alternate materials. For example, a single sapphire tube utilized for the first housing portion 22 can allow for wireless charging of the battery 30 even when the IMD 12 is implanted within a patient.

In one or more embodiments, at least one of the first and second portions 22, 24 of the housing 14 can include a substantially transparent material. As used herein, the phrase "substantially transparent" means that the substrate transmits greater than 50% of electromagnetic radiation incident on the substrate for a selected wavelength or range of wavelengths, assuming no reflection at the air-substrate boundaries. In one or more embodiments, at least one of the first and second portions 22, 24 can be substantially transmissive to electromagnetic radiation having a wavelength of at least 200 nm. In one or more embodiments, at least one of the first and second portions 22, 24 can be substantially transmissive to electromagnetic radiation having a wavelength of greater than 10,000 nm. In one or more embodiments, at least one of the first and second portions 22, 24 can be substantially transmissive to electromagnetic radiation having a wavelength in a range of 200 nm to 10,000 nm. In one or more embodiments, at least one of the first and second portions 22, 24 can be substantially transmissive to at least one of UV light, visible light, or IR light. The substantially transparent material can include at least one of glass, quartz, silica, sapphire, silicon carbide, diamond, or gallium nitride.

Figure 4:
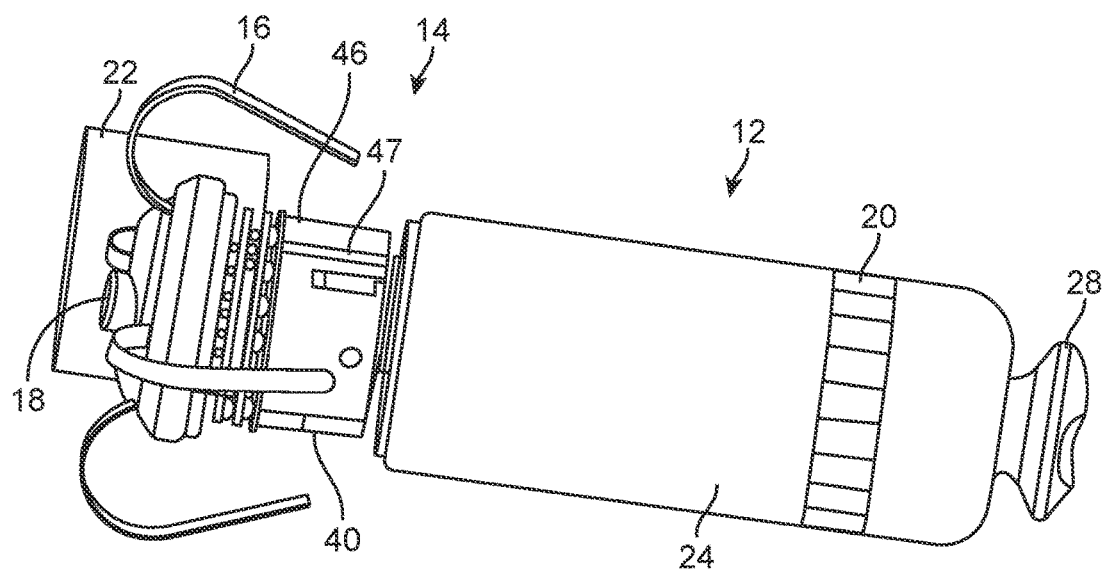
FIG. 4 is a schematic perspective view of the implantable medical device of FIG. 1.

In one or more embodiments, the first housing portion 22 can include a substantially transparent material such that one or more sensors, emitters, or detectors can be disposed within the first housing portion and transmit or receive electromagnetic radiation through such portion. For example, FIG. 4 is a perspective view of the IMD 12 of FIGS. 1-3 with a transparent first portion 22 partially removed for clarity. As shown in FIG. 4, the electronics module 32 is disposed within the first portion 22.

The electronics module 32 can include any suitable elements or components. For example, as shown in FIG. 3, the electronics module 32 includes one or more electronic layers 40 and a feedthrough header assembly 42 electrically connected to the one or more electronic layers 40. The electronics module 32 can also include one or more coils 44 electrically connected to the electronic layers 40.

Figure 5:
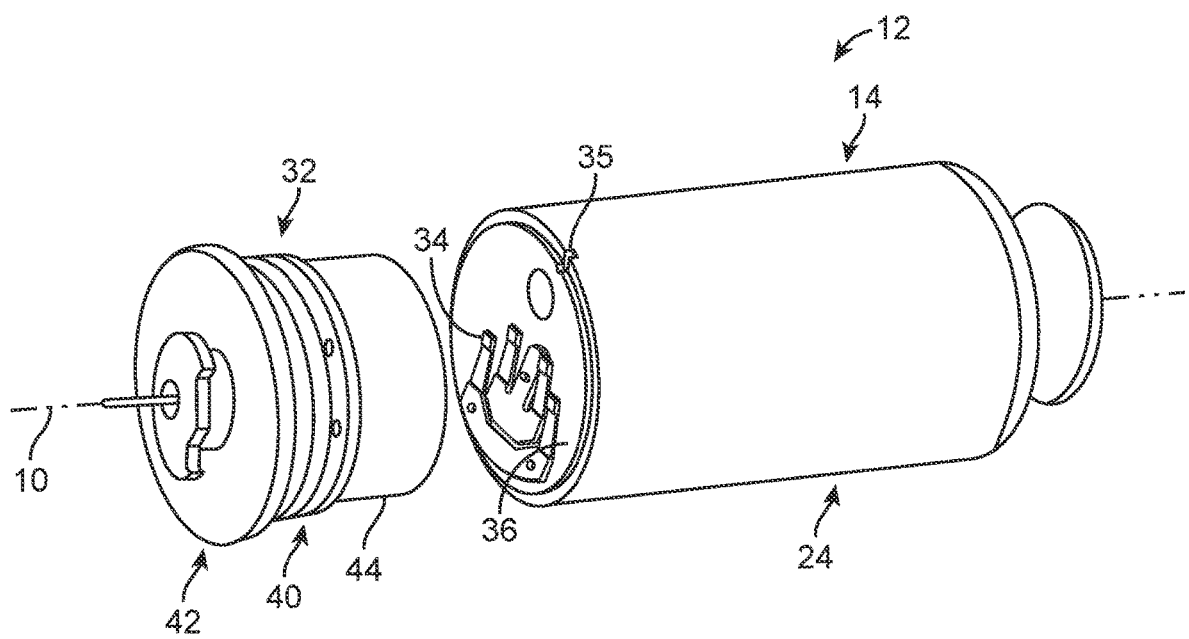
FIG. 5 is a schematic partial exploded view of the implantable medical device of FIG. 1.
Figure 6:
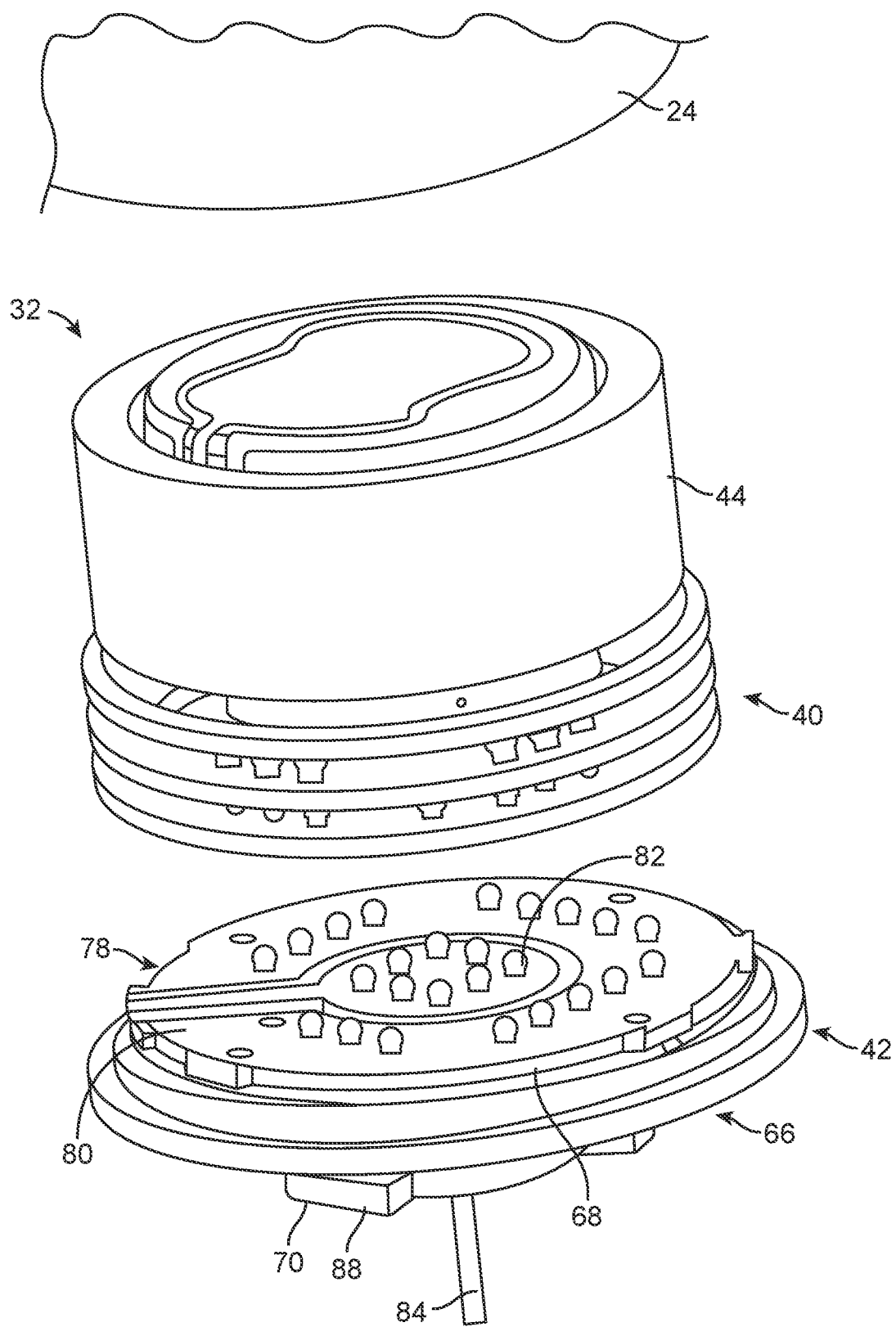
FIG. 6 is a schematic partial exploded view of an electronics module of the implantable medical device of FIG. 1.
Figure 7:
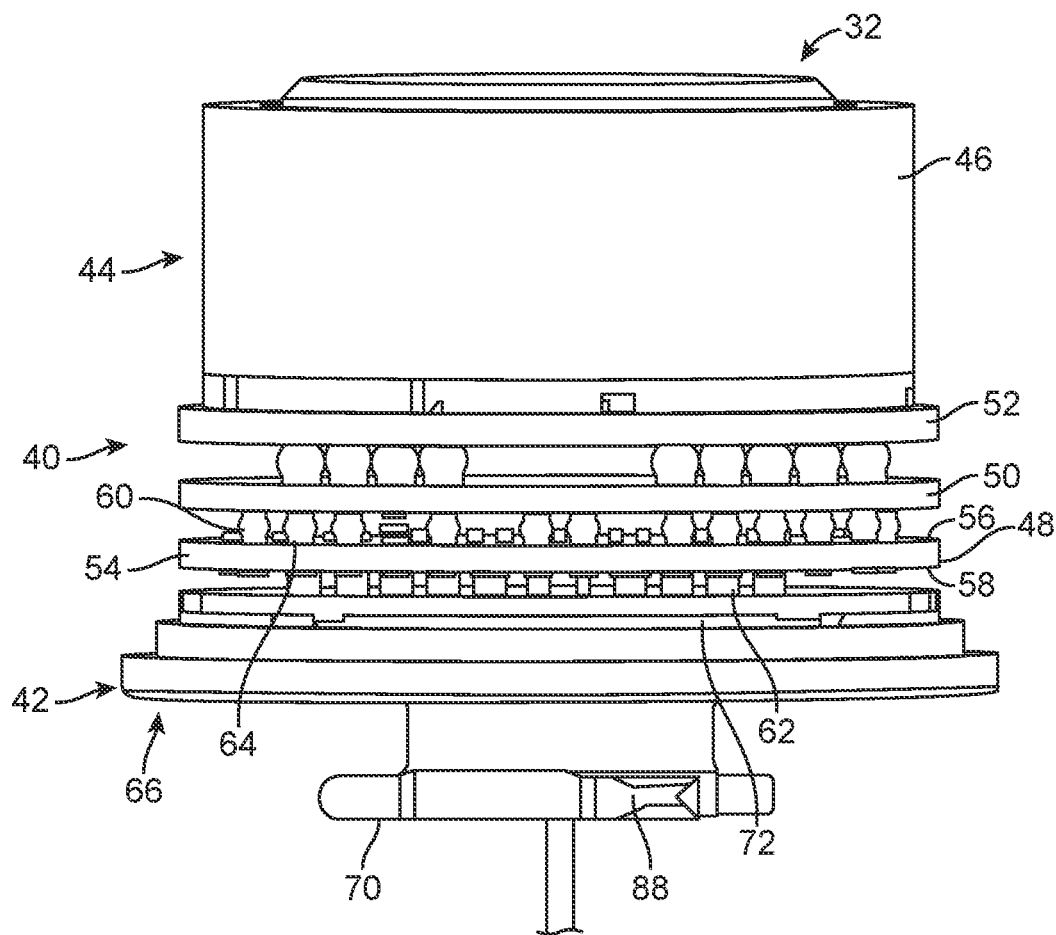
FIG. 7 is a schematic side view of the electronic module of FIG. 6.

FIGS. 5-7 are partially exploded views of the electronics module 32 of the pacing device 12 of FIGS. 1-4. The module 32 includes electronic layers 40 and the feedthrough header assembly 42 electrically connected to the electronic layers.

The electronic layers 40 include a first electronic layer 48, a second electronic layer 50, and a third electronic layer 52. Although illustrated as including three electronic layers, the electronic layers 40 can include any suitable number of layers, e.g., one, two, three, four, five, or more layers. Each layer of the electronic layers 40 can include a substrate. For example, first electronic layer 48 includes a substrate 54 having a first major surface 56 and a second major surface 58.

The electronic layers 40 can be disposed in any suitable relationship relative to the feedthrough header assembly 42 and the battery 30. In one or more embodiments, the electronic layers 40 can be disposed such that they are substantially orthogonal to the longitudinal axis 10 (FIG. 5) of the IMD 12, where the housing 14 of the device extends along the longitudinal axis. For example, the first major surface 56 of the substrate 54 of the first electronic layer 48 is substantially orthogonal to the longitudinal axis 10 of the housing 14. As used herein, the term "substantially orthogonal" means that the longitudinal axis 10 forms an angle with a substrate of one or more of the electronic layers 40 of no greater than 10 degrees.

The electronic layers 40 can be electrically connected together using any suitable technique or techniques. In or more embodiments, one or more of the electronic layers 40 can include one or more conductive vias that are disposed through the respective substrate of one or more of the electronic layers. Further, one or more conductive pads 60 can be disposed on one or more of the conductive layers 40 to provide electrical connections between the feedthrough header assembly 42 and the conductive layers, between one or more of the conductive layers, and between the conductive layers and the electrical contact assembly 34. For example, conductive pad 62 is disposed between (e.g., between conductive surfaces of) the feedthrough header assembly 42 and the first electronic layer 48 to provide an electrical connection between the feedthrough header assembly and the first electronic layer. In one or more embodiments, this connection can be between the housing 14 and the first electronic layer 48 or between one or more of the pins 84 of the assembly and the first electronic layer.

The conductive pads 60 can include any suitable conductive contact, e.g., solder bumps, solder balls, conductive epoxy, braze alloys, etc.

One or more of the electronic layers 40 can include an electronic component disposed on its respective substrate. For example, first electronic layer 48 includes electronic component 64 disposed on the first major surface 56 of the substrate 54. The electronic component 64 can be disposed on at least one of the first major surface 56 or second major surface 58 of the substrate 54. Any suitable number of electronic components can be disposed on one or both major surfaces 56, 58 of the substrate 54. Further, the electronic component 64 can be electrically connected to one or more additional electronic components disposed on the substrate 54 or on the second or third electronic layers 50, 52 using any suitable technique or techniques. In one or more embodiments, the electronic component 64 can be disposed on a patterned conductive layer (not shown) disposed on the substrate 54 using any suitable technique or techniques. One or more conductive vias can be disposed between the first and second major surfaces 56, 58 of the substrate 54 to provide one or more conductive pathways between the patterned conductive layer and other elements or components disposed on an opposite side of the substrate 54 from the electronic component. Further, one or more conductive pads 60 can be directly connected to the electronic component 64 to electrically connect the component to one or more additional components or devices.

Electrically connected to one or more of the electronic layers 40 is the coil 44. Such coil 44 can include any suitable number of coils disposed on or within a housing 46 and one or more electronic components also disposed within the housing. The coil 44 can be utilized to inductively couple the IMD 12 with an external inductive charging system for charging the device when it is implanted within the body of the patient 4 or for telemetry or other types of communication with a transceiver that is external to the patient's body. The coil 44 can be electrically connected to the electronic layers 40 using any suitable technique or techniques. Further, the coil 44 can be electrically connected, e.g., to electronic layer 52 using any suitable technique or techniques. The housing 46 of the coil 44 can provide one or more electrical pathways between the battery 30 and the electronic layers 40 using any suitable technique or techniques. In one or more embodiments, one or more conductors 47 (FIG. 4) can be disposed on or within the housing 46 to provide one or more of these electrical pathways.

Also electrically connected to one or more of the electronic layers 40 is the feedthrough header assembly 42. As shown in FIG. 6, the assembly 42 includes a header 66 that has an inner surface 68 and an outer surface 70. The assembly 42 further includes a dielectric substrate 72 (FIG. 9) that has a first major surface 74 and a second major surface 76. The second major surface 76 of the dielectric substrate 72 is disposed adjacent to the inner surface 68 of the header 66. As used herein, the term "adjacent to the inner surface" means that an element or component is disposed closer to the inner surface 68 of the header than to the outer surface 70 of the header.

The assembly 42 can take any suitable shape or shapes and have any suitable dimensions. In one or more embodiments, the assembly 42 can include an elliptical cross-section in a plane substantially parallel to a first major surface 74 of a dielectric substrate 72.

The assembly 42 further includes one or more patterned conductive layers 78 disposed on the first major surface 74 of the dielectric substrate 72. The patterned conductive layer 78 includes a first conductive portion 80 and a second conductive portion 82 electrically isolated from the first conductive portion. The assembly 10 also includes a feedthrough pin 84 electrically connected to the second conductive portion 82 of the patterned conductive layer 78 and disposed within a via 86 (FIG. 8) that extends through the dielectric substrate 72 and the header 66. The feedthrough pin 84 extends beyond the outer surface 70 of the header 66.

The header 66 can have any suitable dimensions and take any suitable shape or shapes. Further, the header 66 can include any suitable material or materials, e.g., at least one of titanium, copper, niobium, tantalum, or alloys thereof. In one or more embodiments, the header 66 is electrically conductive.

Figure 10:
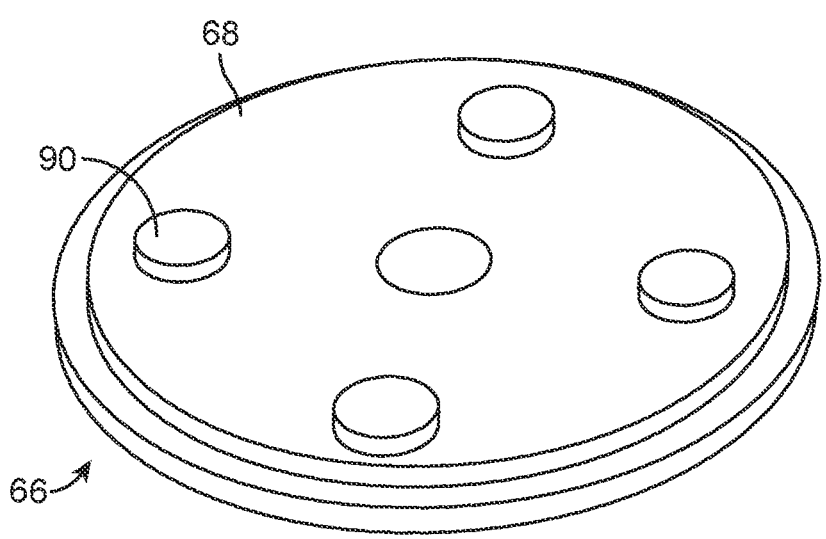
FIG. 10 is a schematic perspective view of a header of the feedthrough header assembly of FIG. 8.

The header 66 can include a flange 88 that at least in part forms the outer surface 70 of the header. The flange 88 can be adapted to connect the header 66 to the end cap 26 (FIG. 2). Further, the header 66 can include one or more conductive projections 90 (FIG. 10), where each extends from the inner surface 68. The conductive projections 90 can take any suitable shape or shapes and have any suitable dimensions. Further, the header 66 can include any suitable number of conductive projections 90, e.g., one, two, three, four, five, or more conductive projections. The conductive projections 90 can be formed integrally with the header 66. In one or more embodiments, the conductive projections 90 can be deposited onto or connected to the inner surface 68 of the header 66 using any suitable technique or techniques.

The conductive projections 90 are electrically connected to the header 66. In one or more embodiments, one or more of the conductive projections 90 is adapted to electrically connect the header 66 to the first conductive portion 80 of the patterned conductive layer 78. In one or more embodiments, one or more conductive projections 90 extend from the inner surface 68 of the header 66 through the dielectric substrate 72 to the first conductive portion 80 of the patterned conductive layer 78. Any suitable technique or techniques can be utilized to electrically connect the conductive projections 90 to the first conductive portion 80, e.g., soldering, welding, conductive epoxy, etc.

Figure 9:
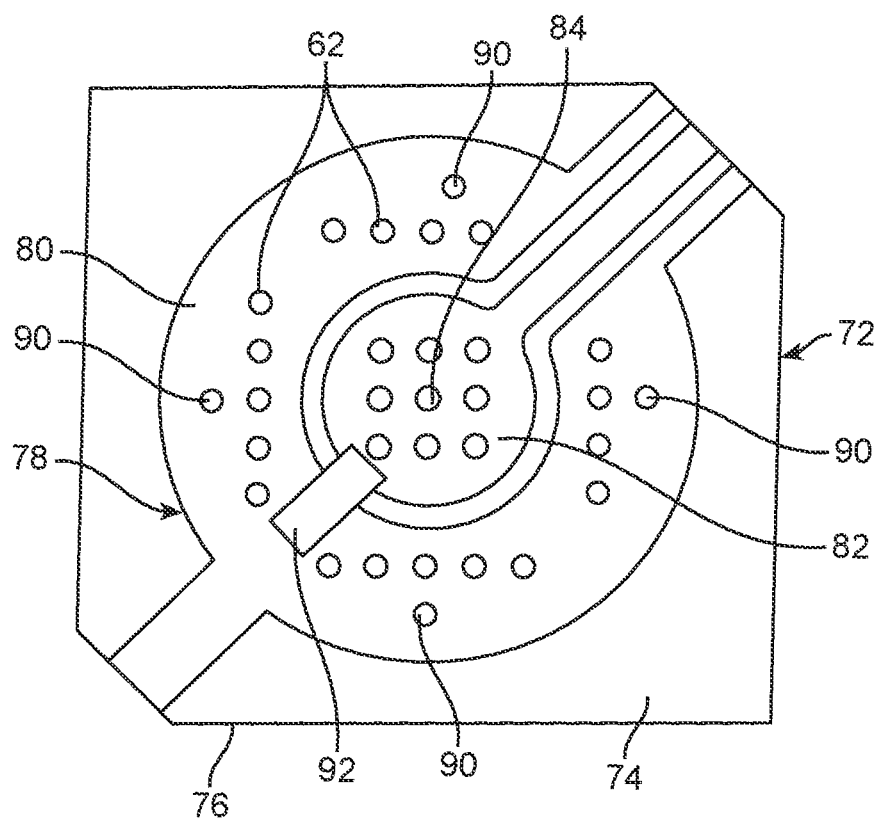
FIG. 9 is a schematic plan view of a dielectric substrate and a patterned conductive layer of the feedthrough header assembly of FIG. 8.

Disposed adjacent to the inner surface 68 of the header 66 is the dielectric substrate 72. The dielectric substrate 72 can take any suitable shape or shapes. In one or more embodiments, the header 66 can be connected to the dielectric substrate 72 using any suitable techniques, e.g., adhering (e.g., with a pressure-sensitive adhesive), mechanically fastening, bonding, etc. In one or more embodiments, the dielectric substrate 72 can take a substantially rectangular shape that can extend beyond an outer perimeter of the header 66 as shown in FIG. 9, and one or more portions of the dielectric substrate can be removed during manufacturing such that the dielectric substrate takes an elliptical shape as shown in FIG. 6 to conform with the shape of the header 66. Further, the dielectric substrate 72 can include any suitable dielectric material or materials, e.g., at least one of polyimide, polyester, or mylar. Further, the dielectric substrate 72 can include one or more layers of material that are connected together using any suitable technique or techniques.

Disposed on the first major surface 74 of the dielectric substrate 72 is the patterned conductive layer 78. The patterned conductive layer 78 can take any suitable shape or shapes and have any suitable dimensions. Further, the patterned conductive layer 78 can include any suitable conductive material or materials, e.g., at least one of titanium, copper, niobium, or platinum. The patterned conductive layer 78 can be disposed on the first major surface 74 of the dielectric substrate 72 using any suitable technique or techniques, e.g., chemical vapor deposition, plasma deposition, photo-etched conductors attached by adhesive. Further, the patterned conductive layer 78 can be patterned using any suitable technique or techniques, e.g., photo etching.

The feedthrough header assembly 42 can further include one or more conductive pads 62 disposed on the patterned conductive layer 78 such that the patterned conductive layer is between the conductive pad and the dielectric substrate 72. Any suitable number of conductive pads 62 can be disposed on the patterned conductive layer 78. The conductive pads 62 can include any suitable conductive structure, e.g., at least one of a solder bump, solder paste, conductive epoxy, or conductive joint. Further, the conductive pads 62 can be adapted to electrically connect the patterned conductive layer 78 to one or more of the electronic layers 40 of the electronics module 32. In one or more embodiments, the conductive pads 62 can electrically connect at least one of the first conductive portion 80 or the second conductive portion 82 (or any suitable number of additional conductive portions) of the patterned conductive layer 78 to the first electronic layer 48 of the electronic layers 40. In one or more embodiments, the conductive pads 62 can provide redundant connections between the patterned conductive layer 78 and other components of the IMD 12, e.g., one or more of the electronic layers 40.

The conductive pads 62 can be disposed on the patterned conductive layer 78 using any suitable technique or techniques, e.g., sputtering, plating, etc. In one or more embodiments, the conductive pads 62 can be integral with the patterned conductive layer 78, i.e., the conductive pads and the patterned conductive layer are formed as a single entity.

Figure 8:
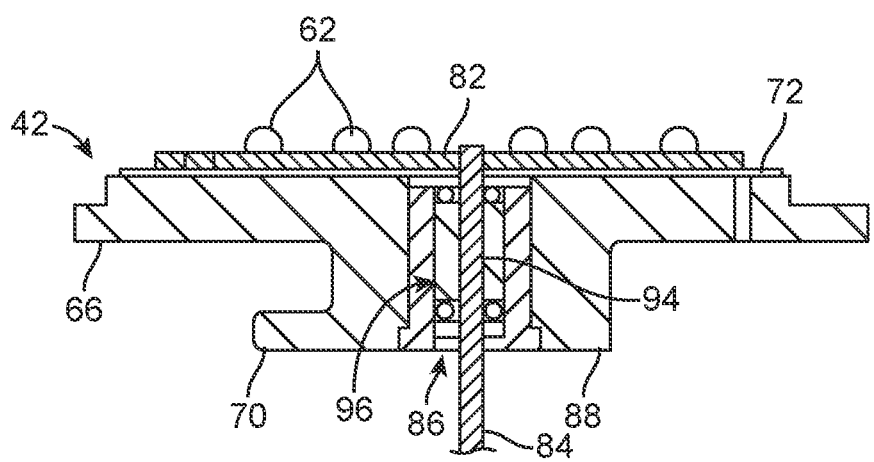
FIG. 8 is a schematic cross-section view of a feedthrough header assembly of the electronics module of FIG. 6.

Electrically connected to the second conductive portion 82 of the patterned conductive layer 78 is the feedthrough pin 84. The feedthrough pin 84 can be electrically connected to the second conductive portion 82 using any suitable technique or techniques, e.g., welding, soldering, brazing, adhering utilizing a conductive adhesive, etc. In one or more embodiments, the feedthrough pin 84 is electrically connected to the second conductive portion 82 of the patterned conductive layer 78 by a weld joint. Further, in one or more embodiments, the feedthrough pin 84 can extend through the second conductive portion 82 of the patterned conductive layer 78 as shown in FIG. 8.

As mentioned herein, the feedthrough pin 84 is disposed within the via 86 that extends through the dielectric substrate 72 and the header 66. As shown in FIG. 8, insulating material 94 can be disposed between the feedthrough pin 84 and at least a portion 96 of the via 86 disposed through the header 66 such that the feedthrough pin is electrically isolated from the header. Any suitable insulating material 94 can be utilized to isolate the feedthrough pin 84 within the via 86, e.g., glass, sapphire, epoxy, or other non-conductive material that provides a seal, etc.

The feedthrough header assembly 42 can further include one or more electronic components. For example, as shown in FIG. 9, the assembly 42 includes one or more filters 92 disposed on the patterned conductive layer 78 in any suitable location. In one or more embodiments, the filter 92 can be electrically connected to at least one of the first conductive portion 80 or the second conductive portion 82 of the patterned conductive layer 78. Further, the filter 92 can be electrically connected to at least one of the first conductive portion 80 or the second conductive portion 82 utilizing any suitable technique or techniques. The filter 92 can include any suitable filter or other electronic component.

Figure 11:
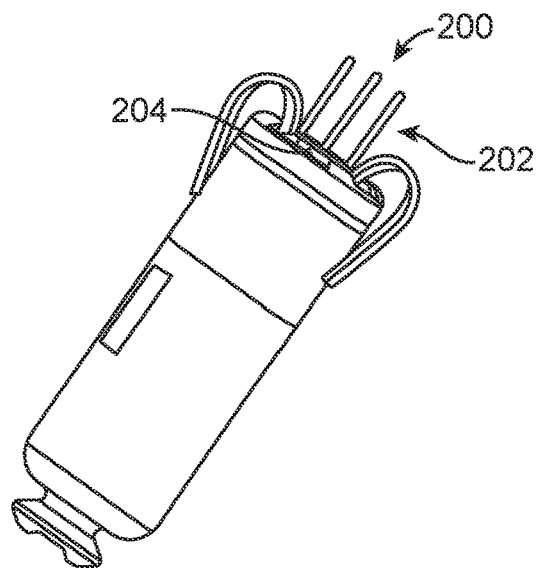
FIG. 11 is a schematic perspective view of another embodiment of an implantable medical device.
Figure 12:
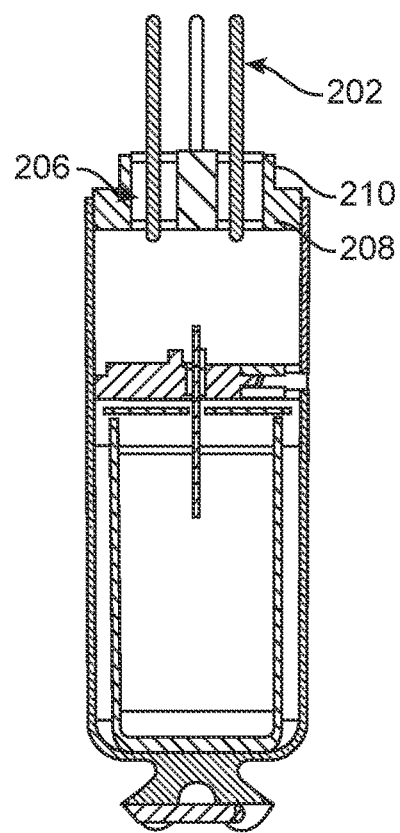
FIG. 12 is a schematic cross-section view of the implantable medical device of FIG. 11.

Although depicted as including one feedthrough pin 84, the feedthrough header assembly 42 can include any suitable number of feedthrough pins, e.g., two, three, four, five, or more feedthrough pins. For example, FIGS. 11-12 are various views of another embodiment of a pacing device 200. All of the design considerations and possibilities of the pacing device 12 of FIGS. 1-10 apply equally to the pacing device 100 of FIG. 11.

One difference between pacing device 200 and pacing device 12 is that device 100 includes four feedthrough pins 202 that extend from an endcap 204 of the device. Each of the feedthrough pins 202 can be electrically connected to a conductive portion of a patterned conductive layer (e.g., second conductive portion 82 of patterned conductive layer 78 of FIG. 6). Further, each of the feedthrough pins 202 can be disposed within a via 206 that extends through a dielectric substrate 208 and a header 210. In one or more embodiments, two or more of the feedthrough pins can be disposed in the same via and electrically isolated using an insulating material. In one or more embodiments, each feedthrough pin 202 can be disposed in its own respective via. Further, each of the feedthrough pins 202 can extend beyond an outer surface of a header as shown in FIG. 8 regarding feedthrough pin 84 and header 66.

Figure 14:
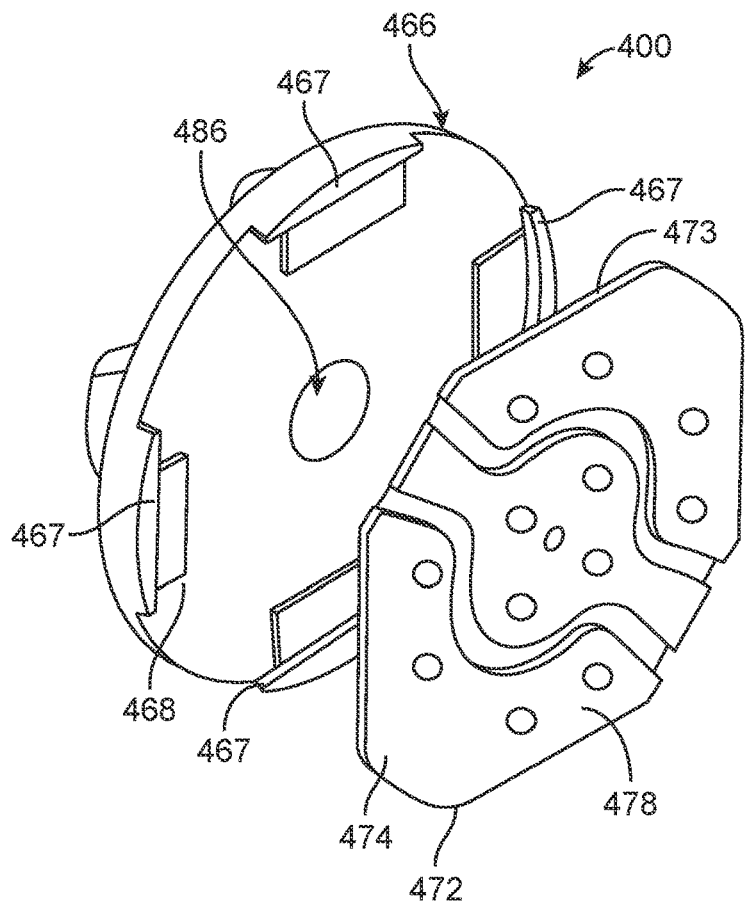
FIG. 14 is an exploded view of another embodiment of a feedthrough header assembly.
Figure 15:
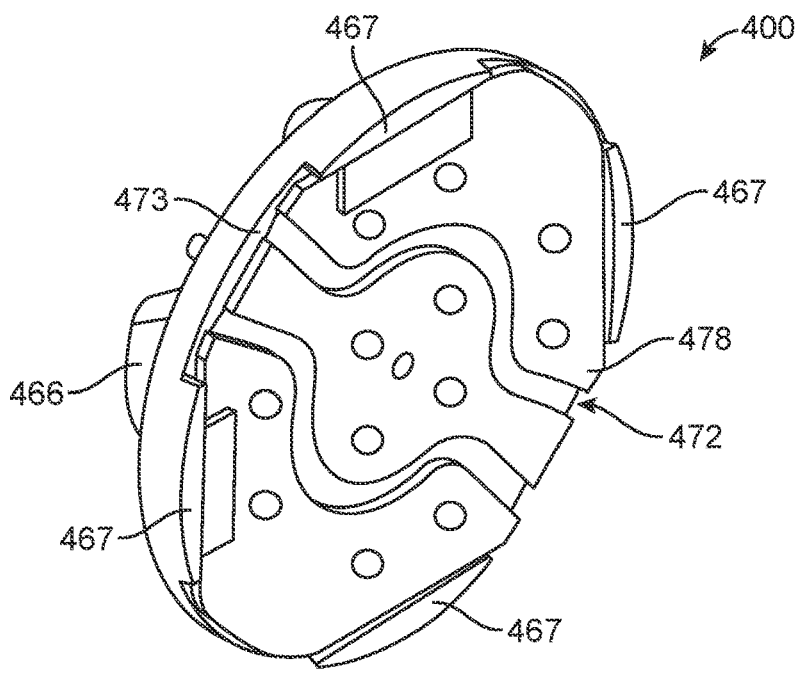
FIG. 15 is a perspective view of the feedthrough header assembly of FIG. 14.

Any suitable technique or techniques can be utilized to connect a dielectric substrate (e.g., dielectric substrate 72 of FIGS. 1-10) to a header (e.g., header 66) such that the dielectric substrate remains disposed in a desired position and orientation. For example, FIGS. 14-15 are schematic exploded and perspective views of another embodiment of a feedthrough header assembly 400. All of the design considerations and possibilities described herein regarding the feedthrough header assembly 42 of FIGS. 1-10 apply equally to feedthrough header assembly 400 of FIGS. 14-15. The assembly 400 includes a header 466 that has an inner surface 468, a dielectric substrate 472 that includes a first major surface 474 and a second major surface (not shown), and a patterned conductive layer 478 disposed on the first major surface of the dielectric substrate. The second major surface of the dielectric substrate 472 is disposed adjacent to the inner surface 468 of the header 466. Although not shown, the assembly 400 can also include a feedthrough pin (e.g., feedthrough pin 84 of FIG. 8) electrically connected to the patterned conductive layer 478, where the feedthrough pin is disposed within a via 486 that extends through the dielectric substrate 472 and the header 468 as is further described herein.

One difference between the assembly 400 of FIGS. 14-15 and the assembly 42 of FIGS. 1-10 is that the header 468 of assembly 400 includes one or more tabs 467 disposed on the inner surface 468 that are adapted to engage one or more edges 473 of the dielectric substrate 472. The dielectric substrate 472 can, therefore, take any suitable shape or shapes in a plane parallel to the first major surface 474 that is adapted to fit within the tabs 467 on the inner surface 468 of the header 466 such that the dielectric substrate is aligned with the header in a desired position and orientation. Further, the tabs 467 of the header 466 can be adapted to retain the dielectric substrate 472 on the inner surface 468 such that the dielectric substrate is fixed in place. The header 466 can include any suitable number of tabs 467. Further the tabs 467 can take any suitable shape or shapes and have any suitable dimensions. The tabs 467 can be integral with the inner surface 468 of the header 466. In one or more embodiments, the tabs 467 are made separately from the header 466 and disposed on the inner surface 468 using any suitable technique or techniques. In one or more embodiments, the tabs 467 of the header 466 can be positioned relative to one or more edges 473 of the conductive layer 478 to facilitate joining of the header and the conductive layer 478 and to electrically connect the tabs and the conductive layer.

Figure 16:
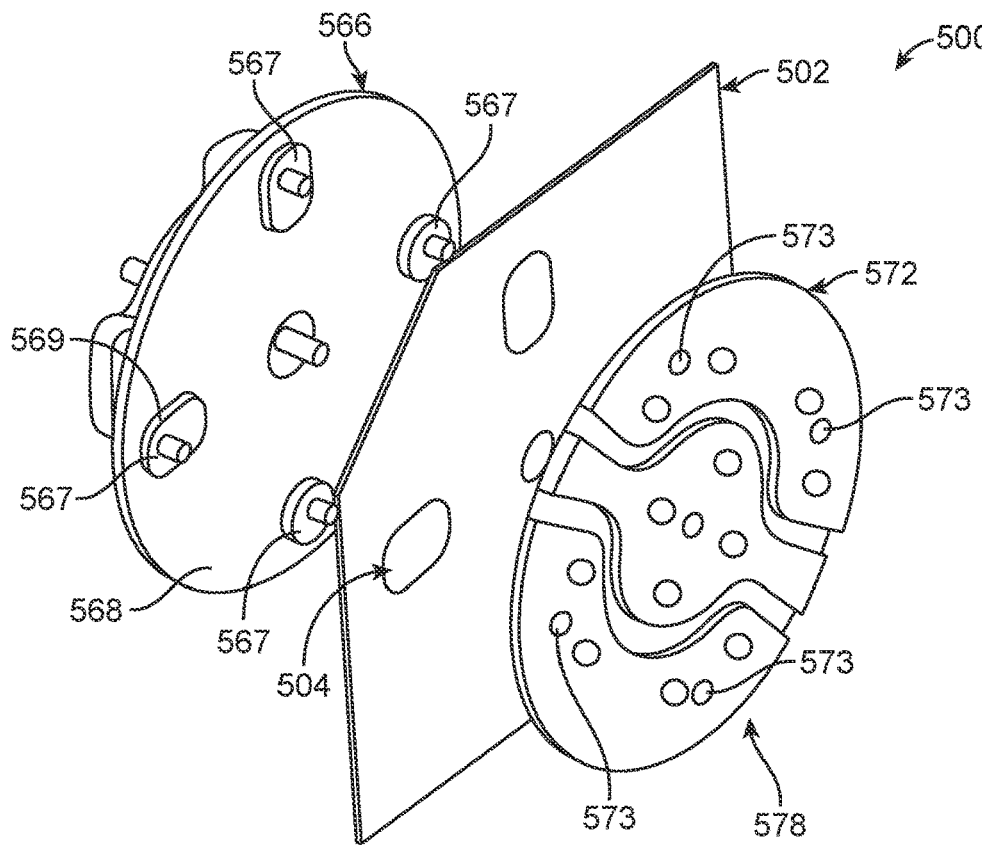
FIG. 16 is a schematic exploded view of another embodiment of a feedthrough header assembly.
Figure 17:
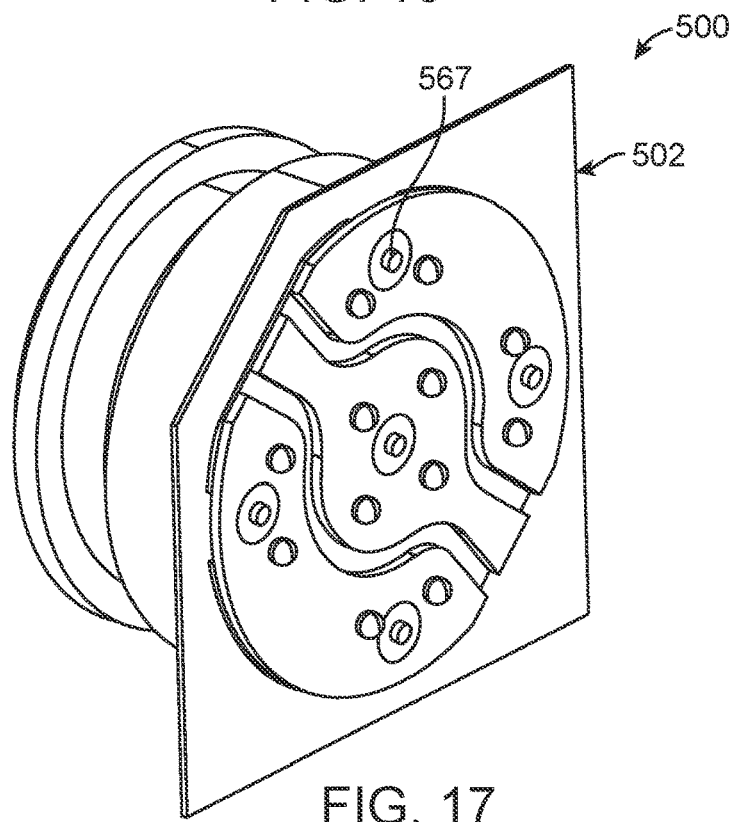
FIG. 17 is a schematic perspective view of another embodiment of a feedthrough header assembly.

FIGS. 16-17 are schematic exploded and perspective views of another embodiment of a feedthrough header assembly 500. All of the design considerations and possibilities described herein regarding the feedthrough header assembly 42 of FIGS. 1-10 and the feedthrough header assembly 400 of FIGS. 14-15 apply equally to the feedthrough header assembly 500 of FIGS. 16-17.

One difference between assembly 500 and assemblies 42 and 400 is that assembly 500 includes one or more posts 567 disposed on inner surface 568 of header 566. The posts 567 are adapted to be inserted through openings 504 of insulating layer 502 and openings 573 of dielectric substrate 572 and patterned conductive layer 578 to fix the dielectric substrate in a desired position and orientation relative to the header. In one or more embodiments, the posts 567 can be connected to at least one of the insulating layer 502, the dielectric substrate 572, or the patterned conductive layer 578 using any suitable technique or techniques. For example, the posts 567 can be welded to the patterned conductive layer 578 such that the dielectric substrate 572 and the insulating layer 502 are retained on the header 566 and the patterned conductive layer is electrically connected to the header 566. In one or more embodiments, one or more posts 567 can include a base 569 having a cross-sectional area that is greater than a cross-sectional area of the post. Such base 569 can be adapted to position the insulating layer 502 on the header 566 by inserting the base into the opening 504 of the insulating layer 502.

The header 566 can include any suitable number of posts 567. Further, the posts 567 can take any suitable shape or shapes and have any suitable dimensions. In one or more embodiments, the dimensions of the posts 567 and the openings 573 in the dielectric substrate 572 and patterned conductive layer 578 can be selected such that the openings are friction-fit onto the posts. Further, the posts 567 can be disposed on the inner surface 568 of the header 566 using any suitable technique or techniques. The posts 567 can be integral with the inner surface 568 of the header 566. In one or more embodiments, the posts 567 are manufactured separately and connected to the inner surface 568 using any suitable technique or techniques.

Another difference between assembly 500 and assemblies 42 and 400 is that assembly 500 includes the insulating layer 502 disposed between the inner surface 568 of the header 566 and the dielectric substrate 572. The insulating layer 502 can include any suitable non-conductive material or materials, e.g., polyimide, polyester, mylar, or similar insulating material. Further, the insulating layer 502 can take any suitable shape or shapes and have any suitable dimensions. In one or more embodiments, at least one of the shape or dimensions of the insulating layer 502 can be selected to provide a barrier to molding, potting, or underfill material that can be disposed over the dielectric substrate 572 and the patterned conductive layer 578 such that the potting material does not come in contact with the header 566.

Figure 18:
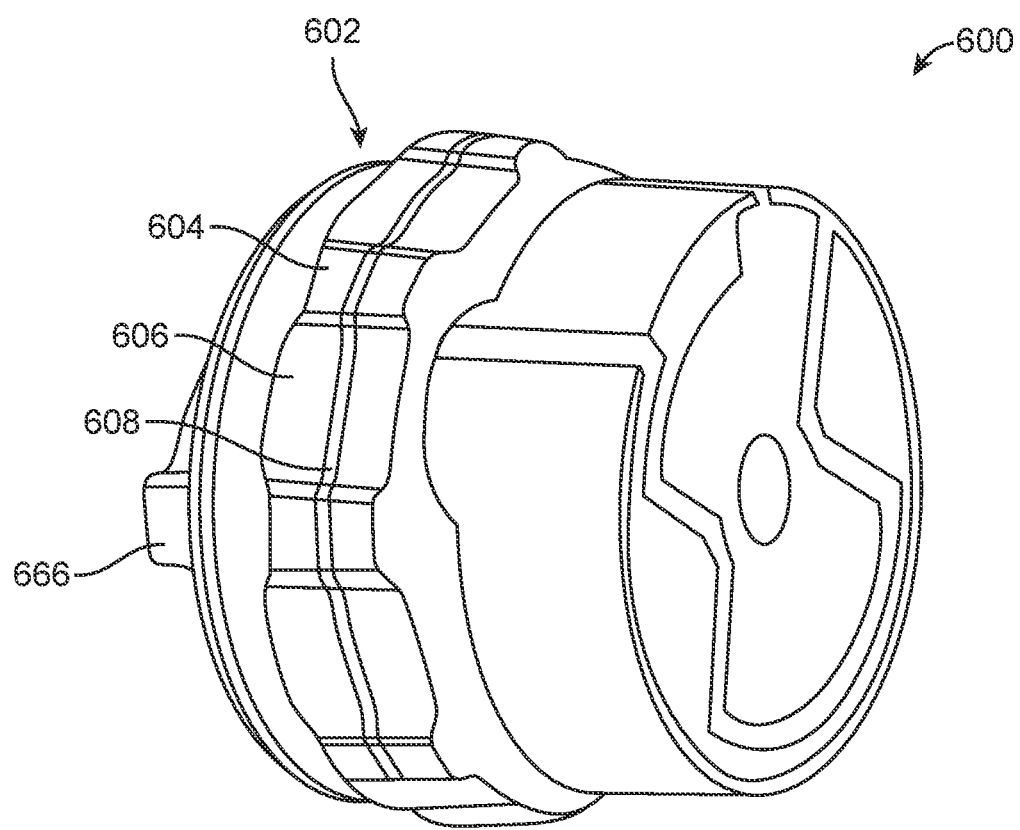
FIG. 18 is a schematic perspective view of another embodiment of an electronics module.

As mentioned herein, the insulating layer 502 can act as a barrier to prevent potting material from contacting the header 566. For example, FIG. 18 is a schematic perspective view of another embodiment of an electronics module 600. All of the design considerations and possibilities described herein regarding electronics module 32 of FIGS. 1-10 apply equally to electronics module 600 of FIG. 18. The electronics module 600 includes potting material 602 disposed over at least a portion of the module 600. The potting material 602 can be utilized to encapsulate a dielectric substrate (e.g., dielectric substrate 72 of FIG. 8) and a patterned conductive layer (e.g., patterned conductive layer 78 of FIG. 9) disposed on the dielectric substrate. Any suitable technique or techniques can be utilized to dispose the potting material 602 over at least a portion of the module 600. In one or more embodiments, the potting material 602 can be disposed over one or more electronic layers (e.g., electronic layers 40 of FIG. 7) to encapsulate such layers. Although not shown, the module 600 can also include an insulating layer (e.g., insulating layer 502 of FIGS. 16-17) to prevent the potting material 602 from contacting a header 666 of the module.

Figure 13:
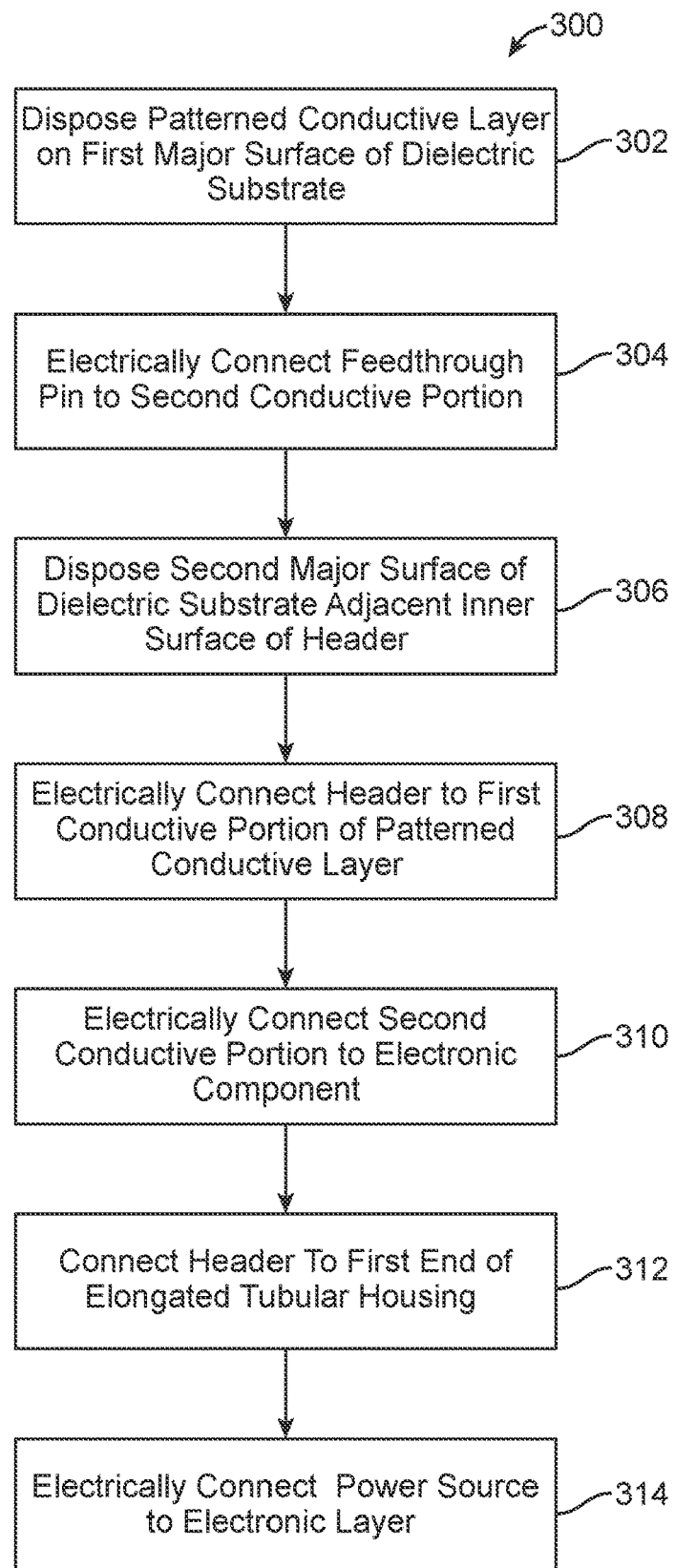
FIG. 13 is a flowchart of one embodiment of a method of forming the implantable medical device of FIG. 1.

The potting material 602 can include any suitable non-conductive material or materials, e.g., epoxy, adhesive, or suitable thermoplastic material. Further, the potting material 602 can be formed into any suitable shape or shapes using any suitable technique or techniques. As shown in FIG. 18, standoffs 604 are formed into the potting material 602. Such standoffs 604 can prevent one or more conductive portions of the electronics module 600 from contacting a housing that encloses the module and potentially forming one or more electrical failure paths. Any suitable number of standoffs 604 can be formed in the potting material 602. The standoffs 604 can take any suitable shape or shapes and have any suitable dimensions. Further, the standoffs 604 can be formed in the potting material 602 using any suitable technique or techniques, e.g., molding to size, laser cutting, machining, waterjet cutting, etc. One or more valleys 606 may be formed between standoffs 604. Electrical traces 608 in the valleys of the electronic layers disposed within the potting material 602 can be utilized as testing traces for testing the electronic layers The various embodiments of pacing devices, electronic modules, and feedthrough header assemblies described herein can be manufactured utilizing any suitable technique or techniques. For example, FIG. 13 is a flowchart of one embodiment of a method 300 for forming the pacing device 12. Although described regarding pacing device 12 of FIGS. 1-10, the method can be utilized to form any suitable implantable medical device.

At 302 the patterned conductive layer 78 can be disposed on the first major surface 74 of the dielectric substrate 72 using any suitable technique or techniques, e.g., deposition followed by etching. The feedthrough pin 84 can be connected to the header 66 and electrically connected to the second conductive portion 82 of the patterned conductive layer 78 at 304 using any suitable technique or techniques, e.g., a weld joint can be formed between the feedthrough pin and the second conductive portion. At 306, the second major surface 76 of the dielectric substrate 72 can be disposed adjacent to the inner surface 68 of the header 66 such that the feedthrough pin 84 is disposed within the via 86 such that the feedthrough pin extends through the dielectric substrate, the header 66, and beyond the outer surface 70 of the header using any suitable technique or techniques.

In one or more embodiments, the header 66 can be electrically connected to the first conductive portion 80 of the patterned conductive layer 78 at 308 using any suitable technique or techniques. In one or more embodiments, conductive projections 90 can be disposed on the inner surface 68 of the header 66 such that the conductive projections extend from the inner surface of the header through the dielectric substrate 72 to the first conductive portion 80 of the patterned conductive layer 78. At 310, the second conductive portion 82 of the patterned conductive layer 78 can be electrically connected to the electronic component 64 of the electronic layer 48 disposed adjacent to the first major surface 74 of the dielectric substrate 72 using any suitable technique or techniques. In one or more embodiments, a conductive pad 62 can be electrically connected to the electronic component 64 through a conductive via disposed in the substrate 54 of the electronic layer 48.

At 312, the header 66 can be connected to the first end 6 of the elongated tubular housing 14 at 312 such that the electronics module 32 (e.g., one or more electronic layers 40) is disposed within the housing. Any suitable technique or techniques can be utilized to connect the header 66 to the first end 6 of the housing 14. In one or more embodiments, the endcap 26 is connected to the header 66, where the endcap defines the first end 6 of the housing 14.

At 314, a power source (e.g., battery 30) can be electrically connected to one or more of the electronic layers 40, e.g., by pressing a first side of the electronics module 32 against the electrical contact assembly 34. The first portion 22 of the housing 14 can be disposed over the electronics module 32 and connected to the second portion 24 of the housing 14 using any suitable technique or techniques, e.g., laser bonding. Further, the end cap 26 can be connected to the header 66 of the feedthrough assembly 42 of the electronics module 32 using any suitable technique or techniques, e.g., welding.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:
1. An implantable medical device comprising:
an elongated housing extending along a longitudinal axis;
a power source; and an electronics module electrically connected to the power source, the electronics module comprising a plurality of electronic layers disposed in the housing and a feedthrough header assembly electrically connected to at least one of the electronic layers;

wherein each electronic layer comprises a substrate having a first major surface, the first major surface being oriented substantially orthogonal to the longitudinal axis;

wherein the feedthrough header assembly comprises:
an electrically conductive header comprising an inner surface and an outer surface;
a dielectric substrate disposed between the inner surface of the header and the electronics module; and
a feedthrough pin that extends through the header in the outward direction beyond the outer surface of the header.

2. The medical device of claim 1, wherein at least one of the electronic layers includes at least one electronic component.

3. The medical device of claim 1, wherein at least one of the electronic layers comprises at least one conductive via.

4. The medical device of claim 3, wherein the at least one conductive via is disposed through the substrate of the electronic layer.

5. The medical device of claim 1, wherein each electronic layer is adjacent to at least one other of the plurality of electronic layers.

6. The medical device of claim 5, wherein one of the plurality of electronic layers is adjacent to the feedthrough header assembly.

7. The medical device of claim 1, further comprising an electrode configured for contact with tissue of a patient, wherein the feedthrough header assembly provides an electrical connection between the electrode and the electronic layers.

8. The medical device of claim 7, wherein the feedthrough header assembly provides a connection between an end cap and the housing, wherein the electrode extends from the end cap.

9. The medical device of claim 7, further comprising a fixation element configured to retain the electrode in contact with cardiac tissue.

10. The medical device of claim 9, wherein the fixation element comprises tines or a helix.

11. The medical device of claim 1, wherein the feedthrough pin is electrically isolated from the header.

12. The medical device of claim 1, wherein each of the electronics layers defines a perimeter, wherein the perimeters of the electronics layers are uniform.

13. The medical device of claim 12, wherein the perimeters of the electronics layers are aligned so as to form a stack.

14. An implantable medical device comprising:
an elongated housing extending along a longitudinal axis;
an electrode disposed at a distal end of the housing;
a fixation element disposed at the distal end of the housing and configured to retain the electrode in contact with cardiac tissue;
a power source; and
an electronics module electrically connected to the power source and to the electrode, the electronics module comprising:
a plurality of electronic layers disposed in a distal portion of the housing;
potting material disposed over at least a portion of the electronics module; and
one or more standoffs disposed in the potting material, wherein the one or more standoffs are configured to prevent one or more conductive portions of the electronics module from contacting the elongated housing;
wherein each electronic layer comprises a substrate having a first major surface, the first major surface being oriented substantially orthogonal to the longitudinal axis;
wherein each electronic layer is adjacent to at least one other of the plurality of electronic layers.

15. The medical device of claim 14, further comprising a feedthrough header assembly electrically connected to at least one of the electronic layers.

16. The medical device of claim 15, wherein the feedthrough header assembly comprises:
a header comprising an inner surface and an outer surface;
a feedthrough pin that extends through the header in the outward direction beyond the outer surface of the header.

17. The medical device of claim 14, wherein one of the plurality of electronic layers is adjacent to the feedthrough header assembly.

18. The medical device of claim 15, wherein the feedthrough header assembly provides an electrical connection between the electrode and the electronic layers.

19. The medical device of claim 14, wherein at least one of the electronic layers includes at least one electronic component.

20. The medical device of claim 14, wherein at least one of the electronic layers comprises at least one conductive via.

21. The medical device of claim 20, wherein the at least one conductive via is disposed through the substrate of the electronic layer.

22. The medical device of claim 14, wherein the fixation element comprises tines or a helix.

23. The medical device of claim 14, wherein each of the electronics layers defines a perimeter, wherein the perimeters of the electronics layers are uniform.

24. The medical device of claim 23, wherein the perimeters of the electronics layers are aligned so as to form a stack.

* * * * *